United States Patent [19]

Flaugh

[11] Patent Number: 5,385,928
[45] Date of Patent: Jan. 31, 1995

[54] TETRAHYDROBENZ [CD] INDAZOLES, COMPOSITIONS AND USE

[75] Inventor: Michael E. Flaugh, Indianapolis, Ind.

[73] Assignee: Eli Lilly and Company, Indianapolis, Ind.

[21] Appl. No.: 245,316

[22] Filed: May 18, 1994

[51] Int. Cl.$^6$ .................. A61K 31/415; C07D 231/54
[52] U.S. Cl. .................................. 514/403; 548/359.1
[58] Field of Search ...................... 548/359.1; 514/403

[56] References Cited

U.S. PATENT DOCUMENTS

| | | |
|---|---|---|
| 4,576,959 | 3/1986 | Flaugh . |
| 4,983,622 | 1/1991 | Flaugh . |
| 5,026,869 | 6/1991 | Flaugh . |
| 5,039,820 | 8/1991 | Kress et al. . |
| 5,204,340 | 4/1993 | Flaugh et al. . |
| 5,212,319 | 5/1993 | Kress et al. . |
| 5,229,409 | 7/1993 | Flaugh et al. . |
| 5,229,410 | 7/1993 | Flaugh et al. . |
| 5,244,912 | 9/1993 | Booher et al. . |
| 5,302,612 | 4/1994 | Flaugh et al. . |

FOREIGN PATENT DOCUMENTS

| | | |
|---|---|---|
| 3525564 | 2/1987 | Germany . |
| 517732 | 2/1972 | Switzerland . |

OTHER PUBLICATIONS

Ainsworth, *The Indazole Analog of Serotonin*, 70, 5245–5247 (1957).
Bertaccini, *Chemical Abstracts*, 56, 6595d (1961).
Kocjan et al "Chemical Abstracts" vol 107 (1987) No. 211, 742j.

*Primary Examiner*—Robert W. Ramsuer
*Attorney, Agent, or Firm*—Joseph A. Jones; David E. Boone

[57] ABSTRACT

A series of 1,3,4,5-tetrahydrobenz[c,d]indazoles having activities as regulators of serotonin functions, particularly in the brain.

15 Claims, No Drawings

“1”

TETRAHYDROBENZ [CD] INDAZOLES, COMPOSITIONS AND USE

FIELD OF THE INVENTION

This invention relates to the fields of synthetic organic chemistry, pharmaceutical chemistry and the physiology of the central nervous system, and provides tetrahydrobenz[cd]indazoles which are useful in treating conditions requiring regulation of the serotonin function, particularly in the brain.

BACKGROUND OF THE INVENTION

Over the last several years it has become apparent that the neurotransmitter serotonin (5-hydroxytryptamine, 5-HT) is associated directly or indirectly with a number of physiological phenomena, including appetite, memory, thermoregulation, sleep, sexual behavior, anxiety, depression, blood pressure lowering and hallucinogenic behavior [Glennon, R. A., *J. Med. Chem.*, 30, 1 (1987)].

It has been recognized that there are multiple types of 5HT receptors. These receptors have been classified as 5-HT$_1$, 5-HT$_2$, and 5-HT$_3$ receptors with the former being further divided into at least the sub-classes 5-HT$_{1A}$, 5-HT$_{1B}$, 5-HT$_{1C}$, and 5-HT$_{1D}$. The binding affinity of a compound for one or more 5-HT receptors can provide a desirable physiological effect or minimize an undesirable effect. Therefore it is desirable to provide compounds which can bind to 5-HT receptors to act as serotonin agonists and antagonists.

Flaugh in U.S. Pat. No. 4,576,959 (issued 1986) and in European Patent Application 0153083 (published 1985) disclosed a family of 6-substituted-4-dialkylamino-1,3,4,5-tetrahydrobenz-[cd]indoles which are described as central serotonin agonists. Leander in U.S. Pat. No. 4,745,126 (1988) disclosed a method for treating anxiety in humans employing a 4-substituted-t,3,4,5-tetrahydrobenz[cd]indole-6-carboxamide derivative.

Pharmaceutical research has continued to focus on the provision of more active and safer agents for the regulation of the various serotonin functions. The present invention provides a series of new compounds having high potency as agonists for the regulation of serotonin functions.

SUMMARY OF THE INVENTION

This invention relates to a compound of the formula

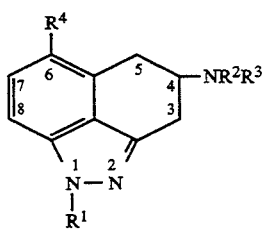

I $R^1$ is hydrogen, $C_1$–$C_4$ alkyl or a blocking group;

$R^2$ is hydrogen, $C_1$–$C_4$ alkyl, $C_3$–$C_4$ alkenyl, cyclopropylmethyl or aryl-($C_1$–$C_4$ alkyl);

$R^3$ is hydrogen, $C_1$–$C_4$ alkyl, $C_3$–$C_4$ alkenyl, or cyclopropylmethyl;

$R^4$ is X-$R^5$, halo, cyano, amino, $C_1$–$C_3$ alkoxy, benzyloxy, acyloxy, nitro, HET or hydroxy;

X is CO, CS or CHOH;

$R^5$ is hydrogen, $C_1$–$C_8$ alkyl, substituted $C_1$–$C_8$ alkyl, $C_1$–$C_4$ alkoxy, $C_1$–$C_4$ alkylthio, aryl, substituted aryl, aryl-($C_1$–$c_4$ alkyl), substituted aryl-($C_1$–$C_4$ alkyl), ($C_3$–$C_7$ cycloakyl)-methyl, $NR^6R^7$, or $C_3$–$C_7$ cycloalkyl;

$R^6$ and $R^7$ are independently hydrogen, $C_1$–$C_4$ alkyl, phenyl-($C_1$–$C_4$ alkyl), phenyl, or together with the nitrogen atom to which they are attached form a $C_3$–$C_5$ heterocyclic ring;

HET is tetrazolyl, substituted tetrazolyl or an aromatic 5- or 6-membered heterocyclic ring, having from 1 to 3 heteroatoms which are the same or different and which are selected from the group consisting of sulfur, oxygen and nitrogen, the rest of the ring atoms being carbon, with the proviso that a 6-membered heterocyclic ring can only contain carbon and nitrogen and with the further proviso that a 5- membered ring can contain no more than one oxygen or one sulfur but not both oxygen and sulfur;

and the pharmaceutically acceptable salts thereof.

The invention also provides pharmaceutical compositions comprising a compound of formula I and a pharmaceutically acceptable excipient, and methods of regulating the functions of serotonin receptors by administering an effective amount of a compound of formula I to a patient in need thereof. Further embodiments of the invention provide methods of regulating the 5-HT$_{1A}$ and 5-HT$_{1D}$ receptors by administering a compound of formula I, and still further embodiments provide methods of treating specific disease states which require regulation of serotonin functions.

DETAILED DESCRIPTION OF THE INVENTION

Throughout the present document, all expressions of amounts, dosages, proportion and percentage will be in weight units unless otherwise stated. All expressions of temperature will be in degrees Celsius.

THE COMPOUNDS

The term "blocking group" is used herein as it is frequently used in synthetic organic chemistry, to refer to a group which will prevent a nitrogen atom from participating in a reaction carried out on some other functional group of the molecule, but which can be removed when it is desired to do so. Such groups are discussed by T. W. Greene in chapter 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973. Examples of such groups include benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-l-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred amino-blocking groups are benzyl (—CH$_2$C$_6$H$_5$), acyl [C(O)R]or SiR$_3$ where R is $C_1$–$C_4$ alkyl, halomethyl, or 2-halo-substituted-($C_2$–$C_4$ alkoxy).

As used herein, the term "alkyl" represents a straight or branched alkyl chain having the indicated number of carbon atoms. For example, "$C_1$–$C_4$ alkyl" groups are methyl, ethyl, n-propyl, isopropyl, n-butyl, sec. -butyl, isobutyl and tert-butyl. "$C_1$–$C_8$ alkyl" groups include those listed for $C_1$–$C_4$ alkyl as well as n-pentyl, 2-methylbutyl, 3-methylbutyl, n-hexyl, 4-methylpentyl, n-heptyl, 3-ethylpentyl, 2-methylhexyl, 2,3 -dimethylpentyl, n-octyl, 3-propylpentyl, 6-methylheptyl, and the like.

The term "$C_3$–$C_4$ alkenyl" refers to olefinically unsaturated alkyl groups such as —$CH_2CH=CH_2$, —$CH_2CH_2CH=CH_2$, —$CH(CH_3)CH=CH_2$ and the like.

The term "aryl" means an aromatic carbocyclic structure having six to ten carbon atoms. Examples of such ring structures are phenyl, naphthyl, and the like.

The term "cycloalkyl" means an aliphatic carbocyclic structure having the indicated number of carbon atoms in the ring. For example, the term "$C_3$–$C_7$ cycloalkyl" means cyclopropyl, cyclobutyl, cyclopentyl, cyclohexyl, and cycloheptyl.

The term "aryl-($C_1$–$C_4$ alkyl)" means an aryl structure joined to a $C_1$–$C_4$ alkyl group. Examples of such groups are benzyl, phenylethyl, α-methylbenzyl, 3-phenylpropyl, α-naphthylmethyl, β-naphthylmethyl, 4-phenylbutyl, and the like.

The $C_1$–$C_8$ alkyl, aryl, and aryl-($C_1$–$C_4$ alkyl) groups can be substituted by one or two moieties. Typical aryl and/or alkyl substituents are $C_1$–$C_3$ alkoxy, halo, hydroxy, $C_1$–$C_3$ alkylthio, nitro, and the like. Moreover, the aryl and aryl-($C_1$–$C_4$ alkyl) groups can also be substituted by a $C_1$–$C_3$ alkyl or a trifluoromethyl group.

In the foregoing, the term "$C_1$–$C_3$ alkoxy" means any of methoxy, ethoxy, n-propoxy, and isopropoxy; the term "halo" means any of fluoro, chloro, bromo, and iodo; and the term "$C_1$–$C_4$ alkylthio" means any of methylthio, ethylthio, n-propylthio, isopropylthio, and the four butylthio's.

Examples of substituted $C_1$–$C_8$ alkyl are methoxymethyl, trifluoromethyl, 6-chlorohexyl, 2 -bromopropyl, 2 -ethoxy-4 -iodobutyl, 3-hydroxypentyl, methylthiomethyl, and the like.

Examples of substituted aryl are p-bromophenyl, m-iodophenyl, p-tolyl, o-hydroxyphenyl, β-(4-hydroxy)-naphthyl, p-(methylthio)phenyl, m-trifluoromethylphenyl, 2-chloro-4-methoxyphenyl, α-(5-chloro)naphthyl, and the like.

Examples of substituted aryl-($C_1$–$C_4$ alkyl) are p-chlorobenzyl, o-methoxybenzyl, m-(methylthio)-α-methylbenzyl, 3-(4'-trifluoromethylphenyl)propyl, o-iodobenzyl, p-methylbenzyl, and the like.

When $R^6$ and $R^7$ combine with the nitrogen atom to which they are attached to form a ring, such rings as piperidine, pyrrolidine, pyridine, 2,3-dihydropyridine, aziridine and the like are provided.

The term "acyl" includes groups derived from both carboxylic and sulfonic acids; i.e., groups of the general structure $R^8Z$ wherein Z is CO or $SO_2$ [indicating radicals derived from carboxylic (COOH) or sulfonic ($SO_2OH$) acids] and $R^8$ is $C_{1-3}$ alkyl, $C_{3-8}$ cycloalkyl, phenyl, naphthyl and substituted phenyl wherein said substituents can be 1 or 2 members of the group halogen (Cl, Br, F), $C_{1-2}$ alkyl, $C_{1-2}$ alkyloxy or other biologically inert substituent. Illustrative acyl moieties include benzoyl, p-tosyl, acetyl, propionyl, isobutyryl, mesyl, ethylsulfonyl, n-propylsulfonyl, p-chlorobenzenesulfonyl, 3,4-methylenedioxybenzoyl, anisoyl, ethoxybenzenesulfonyl, 2,4-xylylsulfonyl, 3,4-dichlorobenzenesulfonyl, cyclopropylcarbonyl, cyclobutylsulfonyl, cycloheptylcarbonyl, cyclohexylcarbonyl, cyclooctylcarbonyl, cyclopentylcarbonyl, α-naphthoyl, β-naphthoyl, α-naphthylsulfonyl, β-naphthylsulfonyl, and the like groups.

The term "aromatic 5- or 6-membered heterocyclic ring" refers to a ring containing from one to three heteroatoms which can be nitrogen, oxygen or sulfur. The 5-membered heterocyclic rings can contain carbon and nitrogen atoms and up to one oxygen or one sulfur but not one of each. In 5-membered rings not containing oxygen or sulfur, one nitrogen can be substituted with either a hydrogen, $C_1$–$C_3$ alkyl, phenyl or ($C_1$–$C_3$ alkyl)-phenyl group. The 6-membered heterocyclic rings can contain carbon and nitrogen atoms only. The 5- or 6-membered rings can have one or two of the carbon atoms in the ring substituted independently with $C_1$–$C_3$ alkyl, halogen, hydroxy, $C_1$–$C_3$ alkoxy, $C_1$–$C_3$ alkylthio, amino, cyano or phenyl. Adjacent carbons in the heterocyclic ring may be connected with a —CH=CH—CH=CH— bridge to form a benzo-fused ring on the heterocycle.

These aromatic 5- or 6-membered heterocyclic rings can be either substituted or unsubstituted and include furan, thiophene, thiazole, oxazole, isoxazole, isothiazole, oxadiazole, thiadiazole, pyridine, pyridazine, pyrimidine, pyrazine, pyrrole, pyrazole, imidazole, and triazole. The heterocyclic ring can be attached to the benzene ring by any carbon in the heterocyclic ring, for example, 2- or 3-furan.

The term "substituted tetrazolyl ring" refers to a tetrazolyl ring system which has a $C_1$–$C_3$ alkyl or phenyl substituent on an available nitrogen atom of such ring system.

As used herein the following terms refer to the structure indicated and include all of the structural isomers:

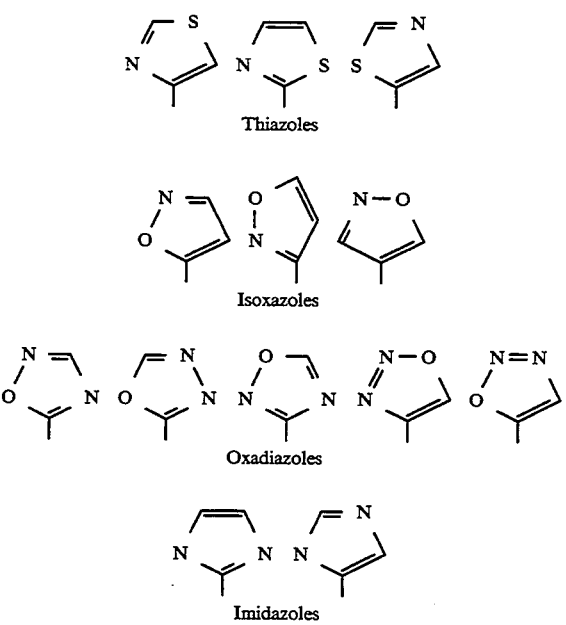

Thiazoles

Isoxazoles

Oxadiazoles

Imidazoles

-continued

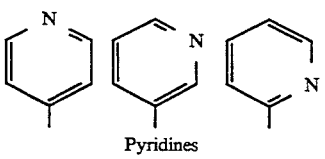
Pyridines

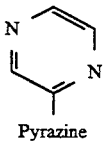
Pyrazine

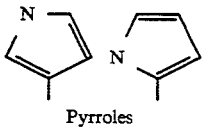
Pyrroles

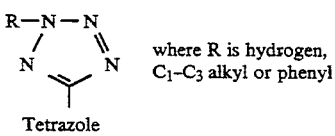
where R is hydrogen, $C_1-C_3$ alkyl or phenyl
Tetrazole

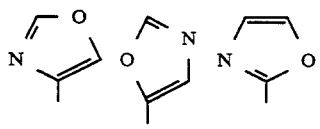
Oxazoles

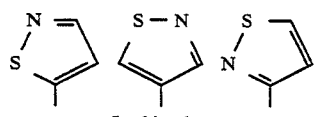
Isothiazoles

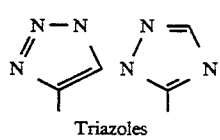
Triazoles

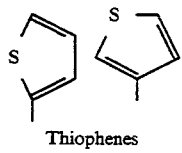
Thiophenes

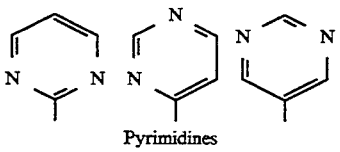
Pyrimidines

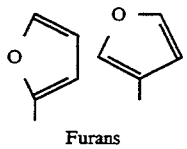
Furans

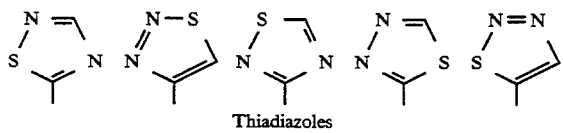
Thiadiazoles

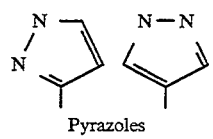
Pyrazoles

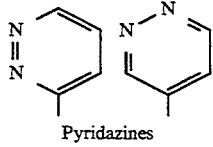
Pyridazines

While all of the compounds of the invention are useful for the purposes taught herein, certain of the present compounds are preferred for such uses. Preferably $R^2$ and $R^3$ are both $C_1-C_4$ alkyl, particularly n-propyl, $R^1$ is hydrogen, and HET is one of the following: isoxazole, oxazole, pyrazole, pyridine, thiazole, furan, thiophene or oxadiazole. Other preferred aspects of the present invention are noted hereinafter.

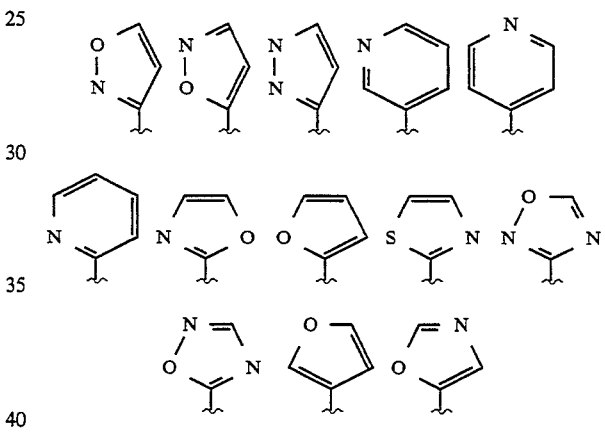

The compounds of the instant invention have at leash one chiral center and therefore at least two stereoisomers can exist for each. A chiral center exists at position 4 of Formula I. If a substituent group contains a chiral center, then additional stereoisomers can exist. Racemic mixtures as well as the substantially pure stereoisomers of Formula I are contemplated as within the scope of the present invention. By the term "substantially pure", it is meant that at least about 90 mole percent, more preferably at least about 95 mole percent and most preferably at least 98 mole percent of the desired stereoisomer is present compared to other possible stereoisomers. R stereoisomers of Formula I are preferred for regulating the $5HT_{1A}$ receptor, and S stereoisomers are preferred for regulating the $5HT_{1D}$ receptor.

The terms "R" and "S" are used herein as commonly used in organic chemistry to denote specific configuration of a chiral center. The term "R" refers to "right" and refers to that configuration of a chiral center with a clockwise relationship of group priorities (highest to second lowest) when viewed along the bond toward the lowest priority group. The term "S" or "left" refers to that configuration of a chiral center with a counter-clockwise relationship of group priorities (highest to second lowest) when viewed along the bond toward the lowest priority group. The priority of groups is based upon their atomic number (heaviest isotope first). A partial list of priorities and a discussion of stereochemistry is contained in the book: *The Vocabulary of Organic Chemistry*, Orchin, et al., John Wiley and Sons Inc., publishers, page 126.

As set forth above, this invention includes the pharmaceutically acceptable salts of the compounds of Formula I. Since the compounds of this invention are amines, they are basic in nature and accordingly react with any number of inorganic and organic acids to form pharmaceutically acceptable salts using acids such as hydrochloric acid, nitric acid, phosphoric acid, sulfuric acid, hydrobromic acid, hydroiodic acid, phosphorous acid and others, as well as salts derived from nontoxic organic acids such as aliphatic mono and dicarboxylic acids, amino acids, phenyl-substituted alkanoic acids, hydroxyalkanoic and hydroxyalkandioic acids, aromatic acids, aliphatic and aromatic sulfonic acids. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, tartrate, isobutyrate, caprate, heptanoate, propiolate, oxalate, malonate, succinate, suberate, sebacate, fumarate, maleate, mandelate, butyne-1,4-dioate, hexyne-1,6-dioate, hippurate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, naphthalene-1-sulfonate, naphthalene-2-sulfonate and mesylate.

The compounds of formula I are all useful and valuable, either as biologically active compounds for therapeutic purposes, or as intermediates for the therapeutic compounds. Those compounds where $R^1$ is a blocking group, and those where $R^4$ is acyloxy or benzyloxy are primarily useful as intermediates, for example. However, certain particular groups of the compounds are of special interest and are preferred, as described below. It will be understood that the limitations set out individually as follows can be combined by the reader to create further, more limited or more expansive groups of preferred compounds.

a) $R^1$ is hydrogen or alkyl;
b) $R^1$ is hydrogen or a blocking group;
c) $R^2$ is hydrogen, alkyl, alkenyl or cyclopropylmethyl;
d) $R^2$ is alkyl or alkenyl;
e) $R^3$ is hydrogen, alkyl or alkenyl;
f) Both $R^2$ and $R^3$ are alkyl;
g) $R^4$ is halo, amino, alkoxy, nitro, HET or hydroxy;
h) $R^4$ is halo, cyano, amino, nitro or HET;
i) $R^4$ is HET;
j) $R^4$ is X-$R^5$;
k) $R^5$ is alkyl, alkoxy, alkylthio or cycloalkyl;
l) X is CO, and $R^5$ is N$R^6R^7$;
m) $R^6$ and $R^7$ are hydrogen, alkyl or phenyl;
n) $R^6$ and $R^7$ form a heterocyclic ring;
o) HET is isoxazolyl, oxazolyl, isothiazolyl, or imadazolyl;
p) HET is 3-isoxazolyl, 5-isoxazolyl, 2-oxazolyl, 5-oxazolyl, 3-isothiazolyl, 5-isothiazolyl, 2-imidazolyl or 4-imidazolyl;
q) A compound of formula I which is a 4-R stereoisomer;
r) A compound of formula I which is a 4-S stereoisomer.

SYNTHESIS

The synthetic methods by which the compounds of formula I are prepared are readily understood and reproduced by the organic chemist. The benz[cd]indazole nucleus of the compounds is most conveniently prepared according to the following Scheme 1:

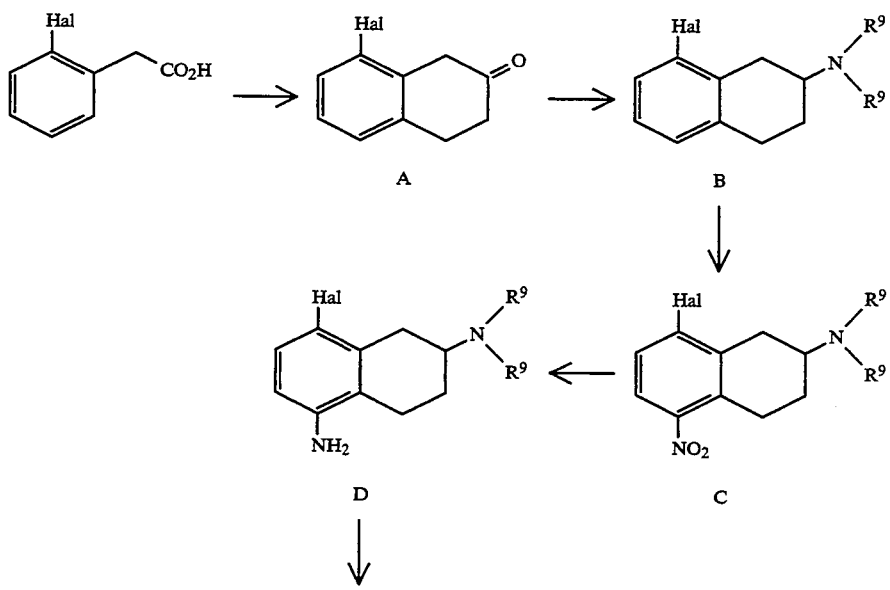

Scheme 1

Scheme 1

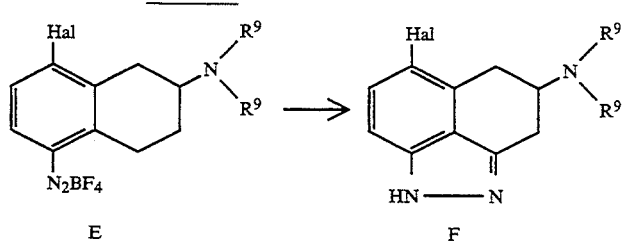

In the above scheme, Hal represents a readily removed halogen atom, usually bromine, but iodine is preferred when transition metal catalyzed substitutions are to be made at the 6-position. The $R^9$ groups may be either $R^2$ and $R^3$ groups, or one of the $R^9$ groups may be an amino blocking group, depending on the identity of the desired final amino substituents. For example, when a preferred dialkylamino compound is to be prepared, it is best to work through the synthesis with a compound where one of the $R^9$ groups is the desired alkyl group, and the other is a blocking acyl group, which at the end of the process may be reduced to the desired alkyl, or may be removed and replaced with the desired $R^2$ or $R^3$ substituent.

Alkyl groups or blocking groups, if needed for later steps in the synthesis, may be placed on the 1-nitrogen by the conventional procedures.

The stereochemistry at the 4-position is fixed at the aminotetralin stage, as will be shown below. The tetralone intermediate A above is prepared by making the acid chloride by heating with excess thionyl chloride, and then reacting with ethylene in the presence of a large amount of aluminum chloride. The tetralone is then reacted with a primary amine such as n-propylamine when the $R^2$ group is to be propyl, followed by reduction with, for example, sodium cyanoborohydride. That intermediate is roughly purified, and the intermediate B is completed by reacting with a reagent that provides the second amino substituent, for example, an acyl blocking group. Such a blocking group may be provided by reaction with the corresponding anhydride in pyridine.

The nitro group of intermediate C is provided by reaction with ammonium nitrate in trifluoroacetic anhydride. This reaction usually prepares a mixture of isomers, and the desired 5-nitroisomer may be separated by chromatography over silica gel, using, for example, a toluene/ethyl acetate gradient. The nitro group is reduced to prepare intermediate C by hydrogenation over nickel or a noble metal catalyst or, when an 8-iodo intermediate is being prepared, preferably by chemical reduction, such as with a reagent derived from a copper or nickel salt and sodium borohydride.

The 5-amino intermediate D is then converted to the corresponding diazonium tetrafluoroborate by the usual reaction with nitrous acid followed by sodium tetrafluoroborate, and the resulting intermediate E is closed by reaction with tetrabutylammonium fluoride at a low temperature. When the desired product is one where $R^4$ is alkoxy, benzyloxy or acyloxy, that substituent may be placed on the starting phenylacetic acid, and carried all the way through the process. When $R^4$ of the final product is to have other definitions, however, the $R^4$ group must be placed in final steps which will be obvious to the organic chemist. For example, the following procedures are used.

According to one route of this process, a 4-amino-6-bromotetrahydrobenz[cd]indazole 1 (Scheme 2) is combined with an equimolar to slight excess amount of potassium hydride in diethyl ether. The reagents are generally combined at a cold temperature, typically in the range of about $-20°$ to about $10°$, preferably at about $0°$. The resulting mixture is cooled to a temperature in the range of about $-100°$ to about $-60°$, preferably about $-78°$, and combined with a lithiating reagent, preferably in at least a two molar excess amount. Suitable lithiating reagents include sec-butyllithium, the preferred t-butyllithium, and other similar organolithium compounds. The reaction is preferably conducted at a temperature in the range of about $-100°$ to about $-20°$, more preferably at about $-60°$ to about $-40°$.

The 1-potassio-4-amino-6-1lithiotetrahydrobenz[c,d]-indazole 2 thus prepared is then contacted with an appropriate electrophile such as L—C(O)$R^5$ wherein $R^5$ is defined above and L is a good leaving group such as chlorine, bromine, methoxy, phenoxy and the like. Typically, a solution of the compound 2 at a temperature in the range of about $-100°$ to about $-60°$, preferably at about $-80°$, is added to a solution of this reagent in a mutual solvent. If an excess amount of the electrophile is employed in the reaction, the 1-amino group is also acylated (i.e., $R^1$ is the acyl group $R^5C(O)$ in compound 3a) and a subsequent hydrolysis reaction is required to provide the free indazole, I. A 1:1 ratio of electrophile to lithiated indazole (compound 2) can be used to minimize acylation of the 1-nitrogen. The reaction is preferably conducted at a temperature in the range of about $-40°$ to about $10°$. The desired compound is purified by quenching the reaction mixture with, for example, ice water, when a 1:1 ratio is used. With a higher ratio in which significant 1-acylation is obtained, the product is hydrolyzed using an acid such as phosphoric acid or a base such as sodium carbonate or sodium hydroxide. The mixture is then washed with a water-immiscible organic solvent. The organic phase is extracted with acid; the aqueous phases are combined and made basic; and the desired compound is extracted with a water immiscible organic solvent. The organic solvent is then concentrated, typically under vacuum, and the desired compound I is further purified, if necessary, by standard procedures.

Scheme 2

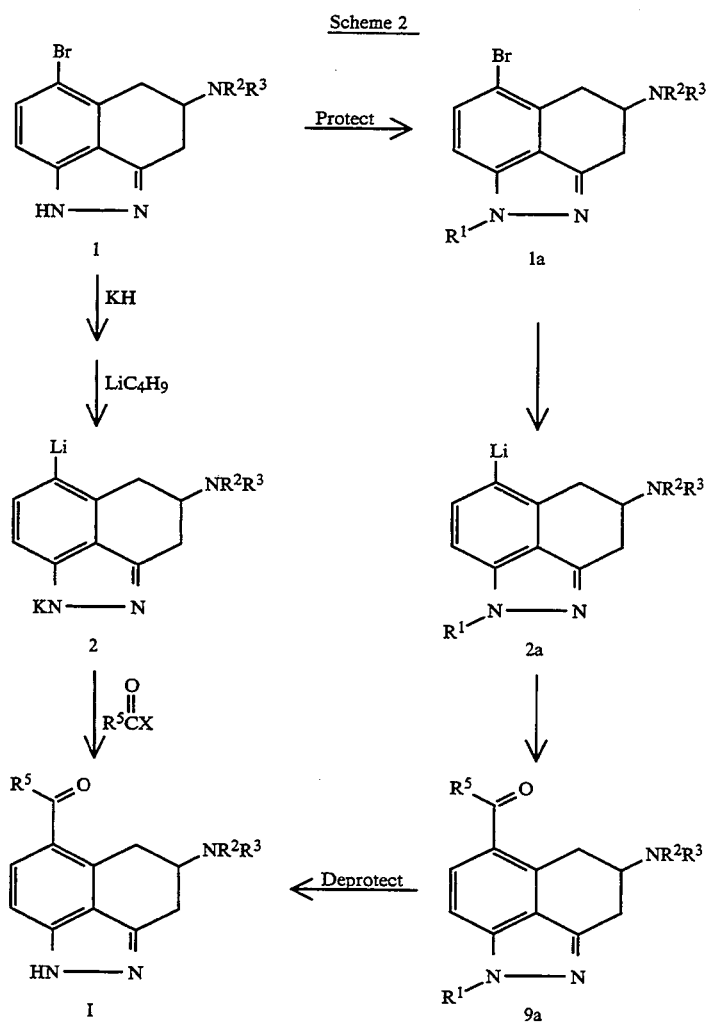

In an alternative route, the 1-nitrogen can be "blocked" or "protected" before initiating the metallation reaction. A blocking group such as $SiR_3$ where R is $C_3$-$C_4$ alkyl, preferably triisopropyl, or phenyl ($C_6H_5$) is preferably used for indazole reactants. Compound 1a is then reacted with a lithiating agent as described above to provide compound 2a. Compound 2a can then be acylated by contacting with a suitable electrophile as described hereinabove. The resulting compound 3a is then deprotected by treatment with a fluoride salt when $R^1$ is $SiR_3$. The desired compound is isolated by standard conditions and purified by crystallization from common solvents or column chromatography over solid supports such as silica gel or alumina.

An alternative synthesis of the compounds I is depicted in Scheme 3 and treats the 6-lithio derivatives 2 and 2a (depicted in Scheme 1) with an aldehyde, $R^5CHO$, to form an alcohol 4 or 4a. Oxidation of the alcohol can be accomplished with oxidants known to those skilled in the art for such purposes such as pyridinium chlorochromate, pyridinium dichromate, dimethylsulfoxide and oxalyl chloride, an aqueous solution of chromic acid and sulfuric acid, and the like. Deprotection of the 1-amino group provides the free amine compounds I.

Scheme 3

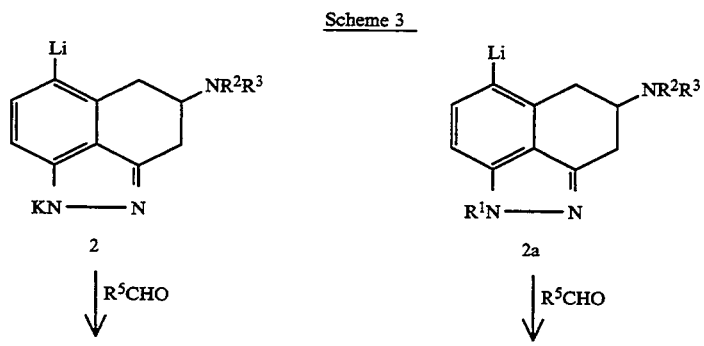

Scheme 3

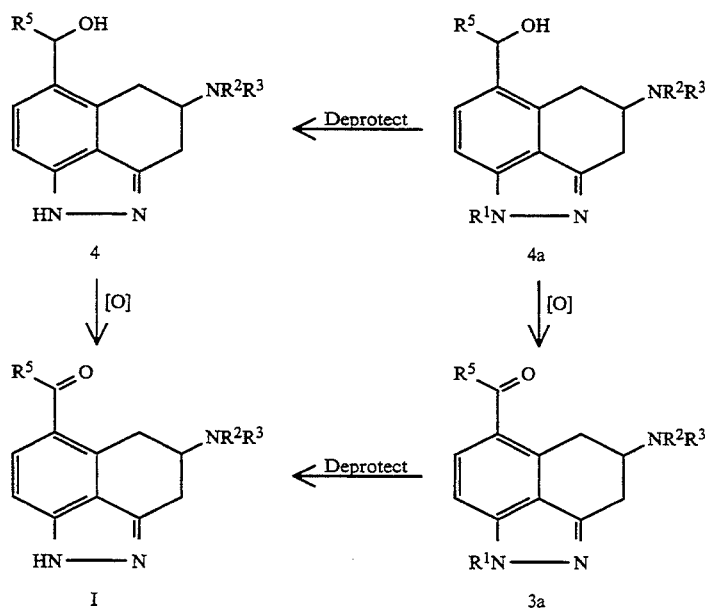

The alcohol intermediates 4 and 4a can alternatively be prepared as depicted in Scheme 4 by addition of an organometallic reagent ($R^5M$) such as an alkyl lithium $R^5Li$ or a Grignard reagent $R^5MgX$ to aldehyde 5 and 5, respectively.

Scheme 4

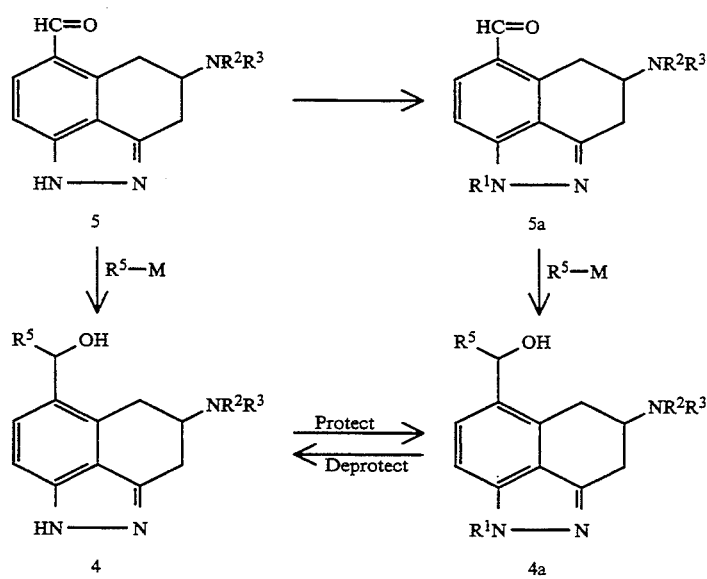

Various routes can be used to prepare aldehydes 5 and 5a. The methods disclosed herein are not intended to be exhaustive and other procedures will be apparent to those skilled in the art. One route involves reacting 6-lithioderivatives 2 and 2a with dimethylformamide followed by aqueous work up. Another method depicted in Scheme 5 involves the preparation of the 6-nitrile derivative 6 followed by reduction and hydrolysis.

Scheme 5

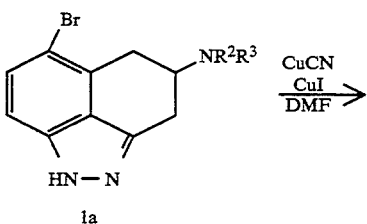

-continued

Scheme 5

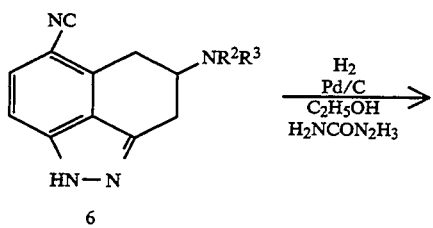

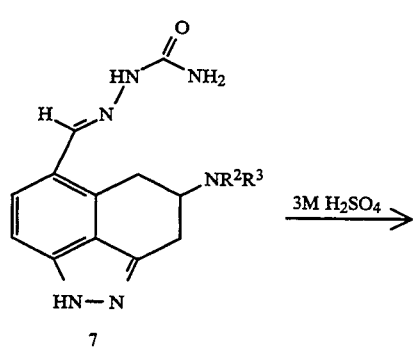

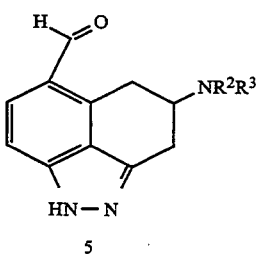

The 6-bromo-derivative 1 a is contacted for example with a mixture of cuprous cyanide and cuprous iodide in dimethylformamide at about 140° or with cuprous cyanide and N-methylpyrrolidone at about 200° The resulting 6-nitrile 6 is hydrogenated over a catalyst such as palladium on carbon in the presence of semicarbazide to provide 6-semicarbazone compound 7. This is hydrolyzed using sulfuric acid to provide aldehyde 5.

In a preferred method of preparation, depicted in Scheme 6, the 6-nitrile derivative 6 (where $R^1$ is a blocking group such as triisopropylsilyl) is contacted with a reducing agent [H]such as diisobutylaluminum hydride. The resulting aldehyde 5a can be contacted with an organometallic reagent such as a Grignard reagent, $R^5$ MgBr, to provide alcohol 4a which is oxidized as described hereinabove to the 1-blocked-6-acyl derivative 3a.

Scheme 6

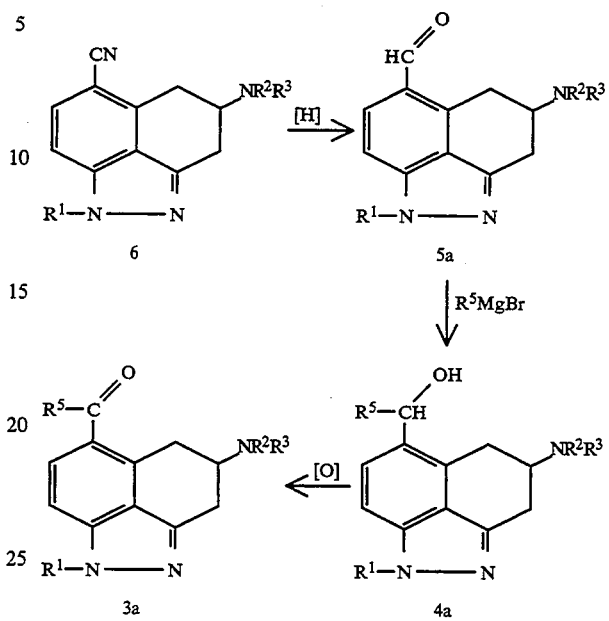

Alternatively, certain compounds of Formula I can be prepared using the 6-iodo derivative 9 as depicted in Schemes 7 and 8 wherein $R^2$, $R^3$ and $R^1$ are as defined hereinabove. The 6-iodo derivative 9 may be prepared as shown in Scheme 1 or by treating the lithio species 2 or 2a of Scheme 2 with an iodinating agent such as iodine, iodine monochloride, or N-iodosuccinimide. In Scheme 7 a method is shown in which a 6-alkyne derivative is prepared. This method provides 6-acyl compounds in which there is a methylene group adjacent to the carbonyl group. In this method the 1-nitrogen can be unprotected (i.e., $R^1$ is hydrogen) or protected with a group (represented by $R^1$) such as a triisopropylsilyl group. This compound 9 is contacted with a palladium catalyst Pd(PPh$_3$)$_4$ [where Ph is phenyl] and the tin alkyne compound $R^{5a}$—C≡C—Sn—(CH$_3$)$_3$. $R^{5a}$ is a $C_1$-$C_7$ alkyl, substituted $C_1$-$C_7$ alkyl, aryl ($C_1$- $C_3$ alkyl), substituted aryl ($C_1$-$C_3$ alkyl), or $C_3$-$C_7$ cycloalkyl. This reaction is normally conducted in a solvent such as toluene at an elevated temperature, for example at about 100°. Typically an excess of the tin alkyne is used along with about 0.25 equivalents of the palladium compound based on compound 9. The 6-alkyne 10 is then contacted with HgSO$_4$ in water to provide the ketone 11. The 1-blocking group can be removed by treatment with a fluoride reagent as described above to provide compound I.

Scheme 7

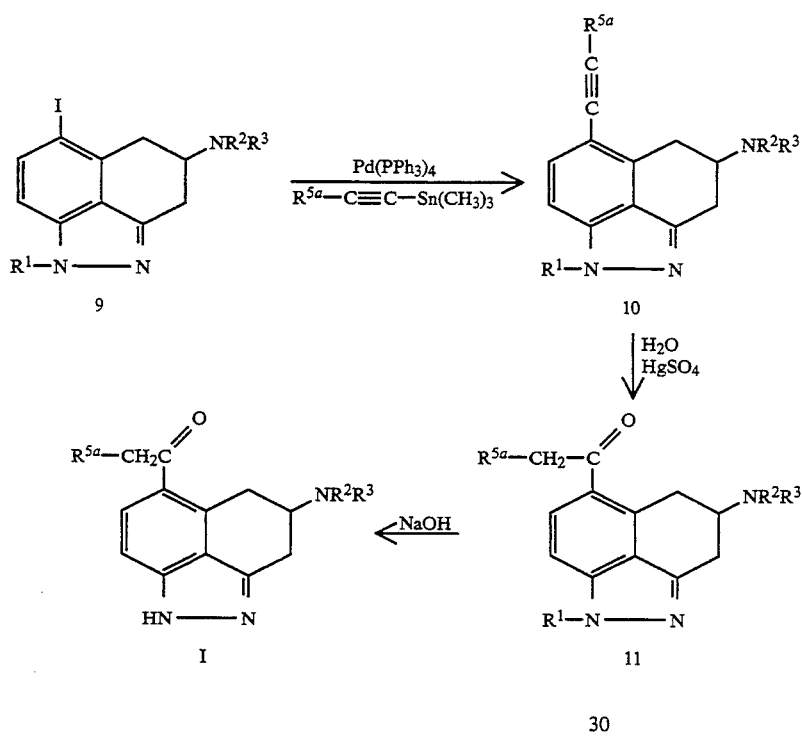

In another preparation method depicted in Scheme 8, the 6-iodo derivative 9 can be used to prepare certain 6-acyl compounds directly. This is accomplished by contacting the 6-iodo compound with a tetraalkyltin complex and carbon monoxide in the presence of a palladium catalyst Pd(PPh$_3$)$_4$ [where Ph is phenyl] as described in the literature for arylhalides. [A. Schoenberg and R. F. Heck, *J. Org. Chem.*, 39, p. 3327 (1974); and A. Schoenberg, I. Bartoletti, and R. F. Heck, *J. Org. Chem.*, 39, P. 3318 (1974)]. Although a blocking group R$^1$ such as diethylcarbamoyl or triisopropylsilyl can be used for this method, the method can also be accomplished when R$^1$ is hydrogen.

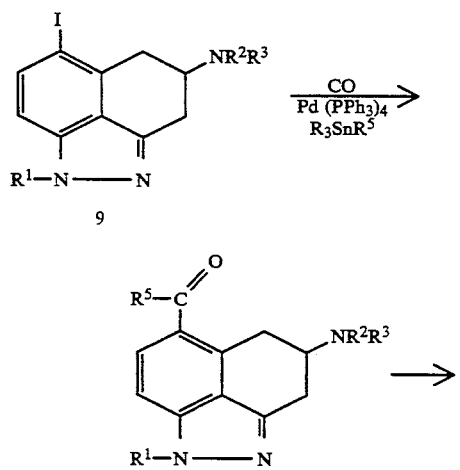

-continued

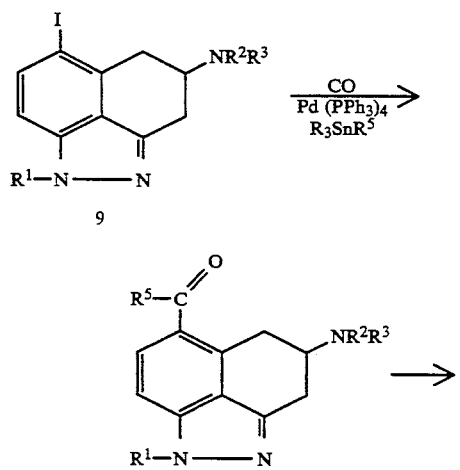

In Scheme 9 a preparative method is depicted in which a vinyl ether is reacted with the 6-iodo derivative 9. R$^1$, R$^2$ and Z are as defined hereinabove. This method provides a 6-(1-alkoxyalkenyl) derivative 12 which can then be hydrolyzed and deprotected to provide the desired compound of Formula I. Alternatively the derivative 12 can be deprotected and then the vinyl group hydrolyzed. The vinyl ethers useful in this method include those in which R$^c$ is a C$_1$–C$_4$ alkyl and Q is hydrogen or an alkyl tin, alkyl or alkoxy boron, zinc halide, or magnesium halide, for example tributyltin. When Q is zinc halide or magnesium halide, it is preferred that R$^1$ be a group such as triisopropylsilyl. R$^a$ and R$^b$ can independently be hydrogen, C$_1$–C$_6$ alkyl, substituted C$_1$–C$_6$ alkyl, aryl, aryl (C$_1$–C$_2$) alkyl, substituted aryl, substituted aryl (C$_1$–C$_2$) alkyl, or C$_3$–C$_7$ cycloalkyl group. The palladium catalyst used can be palladium powder (black) or Pd(PPh$_3$)$_4$ [where Ph is phenyl]. The Pd(PPh$_3$)$_4$ is commonly used with toluene at reflux. The Pd-black can be used with triphenylphosphine in toluene at reflux or in a mixture of acetonitrile and triethylamine at about 100°. Similar reactions are reported in *Bull. Chem. Soc. Jpn.*(1987), 60, 767–768.

Scheme 9

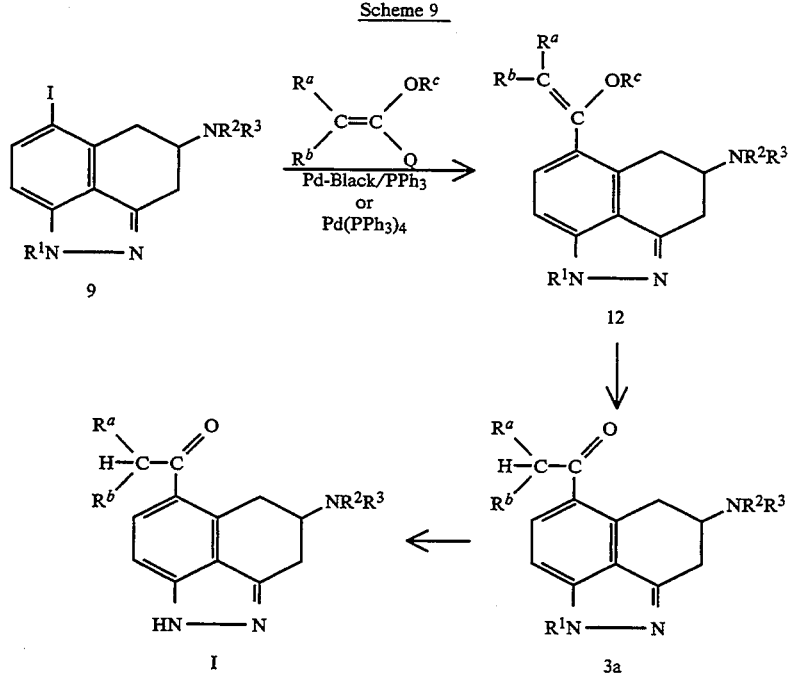

Synthesis of those compounds wherein the R⁴ group is a heterocyclic HET group can be accomplished according to methods set out in full in U.S. Pat. No. 5,244,912, issued Sep. 14, 1993 by Booher et al., which is incorporated by reference herein, and the reader is requested to refer to that issued patent for such synthetic methods.

However, compounds wherein HET is a tetrazole group may additionally be prepared according to the following schemes, wherein the R group has the special definition hydrogen, $C_1$-$C_3$ alkyl or phenyl.

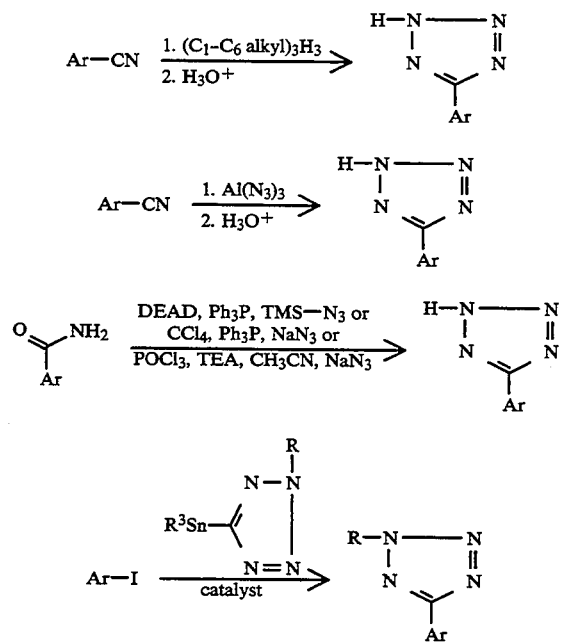

Optically active isomers of the compounds of formula I, where the 4-position is in one of the pure enantiomeric forms, are conveniently produced by isolating the optical isomers of the 8-halo-2-aminotetralin, compound B in Scheme 1. Such isolated enantiomers are prepared by reacting the 2-tetralone, compound B in Scheme 1, with an optically active α-phenethylamine, or another of the well-known optically active groups used in the preparation of stereospecific enantiomers by knowledgeable organic chemists. A particularly useful such group is 4-nitro-α-phenethylamine, in an optically active form, because it has been learned that that group is readily cleaved under mild conditions, compared to those necessary with other conventionally used optically directing groups.

The nitro group is first reduced as with titanium trichloride or lithium aluminum hydride, or by catalytic hydrogenation. A particularly convenient condition for removing the 4-nitrophenylethyl moiety is hydrogenation of the amine monohydrochloride in methanol over a platinum catalyst. The following preparations are provided to illustrate the preparation of optically active enantiomers of the 2-aminotetralin for the convenience of the reader.

PREPARATION 1

Preparation of (R)-2-di-n-propylamino-8-bromo-1,2,3,4-tetrahydronaphthalene and (S)-2-di-n-propylamino-8-bromo-1,2,3,4-tetrahydronaphthalene

A.

N-[1-(4'-Nitrophenyl)ethyl]-N-(8-bromo-2-tetralin)amine

A solution of 50 g of sodium carbonate in 300 mL of water was used to convert 66 g (0.30 mol) of the hydrochloride salt of (S)-(—)-α-methyl-4'-nitrobenzylamine to its free base. The free base was extracted into dichloromethane. This solvent was then removed under vacuum, and the residue was dissolved in 70 mL of acetonitrile. To this solution were added successively 4.5 mL (0.08 mol) of acetic acid, 4.9 g (0.08 mol) of sodium cyanoborohydride, 65 g (0.29 mol) of 8-bromo-2-tetralone (see Example 1), and 20 g of 3A molecular sieves.

The mixture was stirred under nitrogen for 16 h. Another 31.4 g (0.50 mol) of sodium cyanoborohydride was added, followed by 13.5 mL (0.24 mol) of acetic acid. After 4 more hours an addition of 2 mL of acetic acid was made, followed at two hour intervals by two more such additions. After stirring for another 16 h the mixture was filtered, and most of the acetonitrile was removed under vacuum. The residual mixture was poured into cold sodium carbonate solution and extracted with dichloromethane. The extract was washed with sodium chloride solution and dried over sodium sulfate. The dichloromethane was evaporated leaving the crude product as a viscous brown oil. The crude product was taken up in 300 mL of ether and then extracted into a solution of 50 g of tartaric acid in 1.5 L of 30% methanol in water. The aqueous layer was washed twice with fresh ether, then basified with saturated sodium carbonate solution and extracted into dichloromethane. This extract was washed with sodium chloride solution and dried over sodium sulfate. Removal of the solvent under vacuum gave 84.9 g (78% yield) of the product as an amber oil which appeared to be clean by nuclear magnetic resonance analysis.

B. N-[1-(4'-Nitrophenyl) ethyl]-N-(bromo-2-tetralin)propionamides

The compound from Part A (84.9 g, 0.23 mol) was dissolved in 1 L of dichloromethane. This solution was treated with 71 mL (0.51 mol) of triethylamine and then slowly with 42 mL (0.48 mol) of propionyl chloride. The mixture was stirred for 16 h. It was then treated with cold sodium carbonate solution. After stirring vigorously for three hours, the dichloromethane layer was separated. This solution was washed with aqueous tartaric acid solution and then with sodium carbonate solution. After drying over sodium sulfate, the dichloromethane was evaporated leaving 101 g of the crude diastereomeric mixture of amides. The diastereomers were separated by chromatographing in 20–30 g runs on a high performance liquid chromatography system that employed columns containing about 400 g of silica gel ("Prep 500"). The solvent system was a gradient proceeding from pure toluene to 20% ethyl acetate in toluene. The total weight of the first diastereomer (S,R) from the column was 49.6 g. The second diastereomer (S,S) weighed 40.6 g. Both diastereomers were viscous oils. Both contained about 2% toluene. A satisfactory analysis was obtained for the S,S diastereomer after rigorous drying of a small sample. Slightly high carbon and low bromine percentages in the sample of the S,R diastereomer suggested that a trace of solvent had persisted even after drying. Yields of the two diastereomers were approximately 48% and 40%, respectively.

(S,R)-Diastereomer:

OR: $[\alpha]^{25}_D = 9.4°$ (C=10 MeOH) Analysis: Calculated for $C_{21}H_{23}BrN_2O_3$: Theory: C, 58.48, H, 5.38; N, 6.49; Br, 18.53; Found: C, 60.07; H, 5.61; N, 6.28; Br, 17.76. MS: 433 (1), 431 (1), 361 (3), 359 (3), 210 (100), 208(100), 129 (67), 57 (54). UV (EtOH): $\lambda max^{271\ nm}$ ($\epsilon$9600) IR (CHCl3): $\lambda max\ ^{1642\ cm-1}$ (S,S)-Diastereomer:

OR: $[\alpha]^{25}_D - 114°$ (C=10, MeOH) Analysis: Calculated for $C_{21}H_{23}BrN_2O_3$: Theory: C, 58.48; H, 5.38; N, 6.49; Br, 18.53; Found: C, 58.66; H, 5.43; N, 6.37; Br, 18.33. MS: 433 (1), 431 (1), 361 (5), 359 (5), 210(100), 208(100), 129 (99), 57 (92). UV (EtOH): $\lambda max^{273\ nm}$ ($\epsilon$9000) IR (CHCl3): $\lambda max^{1642\ cm-1}$

C. (S,R)-N-[1-(4'-Nitrophenyl)ethyl]-N-(8-bromo-2-tetralin)-1-propylamine

A solution of 49 g (0.114 mol) of the S,R-diastereomer from Part B in 200 mL of tetrahydrofuran was added gradually no 230 mL of ice cooled 1M borane in tetrahydrofuran. The solution was then refluxed under nitrogen for 2 h. After the solution was allowed to cool, it was carefully treated with 100 mL of methanol. This solution was stirred for 1 h. The solvents were evaporated under vacuum, and the residue was taken up in a mixture of 250 mL of dimethylsulfoxide and 30 mL of water. This solution was heated on a steam bath for 1 h. It was then cooled and extracted with dichloromethane. The extracts were washed with sodium chloride solution and dried over sodium sulfate. The dichloromethane was evaporated, and the crude free base was converted to its hydrochloride salt by dissolving in 1 L of diethyl ether and adding 50 mL of 2.6M hydrochloride in ether. The salt was collected and washed with fresh ether. The dried salt, which weighed 50.4 g (97% yield), analyzed satisfactorily.

OR: $[\alpha]^{25}_D + 28°$ (C=10, MeOH) Analysis: Calculated for $C_{21}H_{25}BrN_2O_2 \cdot HCl$: Theory: C, 55.58; H, 5.78; N, 6.17; Cl, 7.81; Br, 17.61; Found: C, 55.32; H, 5.94; N, 5.97; Cl, 7.61; Br, 17.33.

MS: 418(14), 416(15), 389(73), 387(71), 240(61), 238(68), 130 (100), 104 (59). UV (EtOH): $\lambda max^{267\ nm}$ ($\epsilon$10,000)

D. (S,S)-N-[1,(4'-Nitrophenyl)ethyl]-N-(8-bromo-2-tetralin)propylamine

The reduction procedure described in Part C was used to reduce 40 g (0.093 mol) of the S,S diastereomer of the analogous amide. Elemental analysis indicated that the crude hydrochloride salt, obtained in 98% yield, was slighly impure.

OR: $[\alpha]^{25}_D - 94°$ (C=10 MeOH) Analysis: Calculated for $C_{21}H_{25}BrN_2O_2 \cdot HCl$ Theory: C, 55.58; H, 5.78; N, 6.17; Found: C, 55.13; H, 5.94; N, 5.69. MS: 418(21), 416(20), 389(79), 387(78), 240(54), 238(57), 130 (100), 104 (74). UV (EtOH): $\lambda max^{269\ nm}$ ($\epsilon$10,000)

E. (R)-8-Bromo-2-(N-propylamino)tetralin

A solution of 12.5 g (27.6 mmol) of the hydrochloride salt from Part C (S,R diastereomer) in 200 mL of methanol was hydrogenated for 8 h at 40 psi over 0.5 g of sulfided 5% platinum on carbon. After filtering off the catalyst, most of the methanol was evaporated under vacuum without heat. Thorough ether washing of the methanolic slurry that remained afforded 6.55 g (78% yield) of the hydrochloride salt of the title compound. A satisfactory analysis was obtained without further purification.

OR: $[\alpha]^{25}_D + 54°$ (C=8,MeOH) Analysis: Calculated for $C_{13}H_{18}BrN \cdot HCl$ Theory: C, 51.25; H, 6.29; N, 4.60; Br, 26.23 Cl, 11.64; Found: C, 51.48; H, 6.41; N, 4.47, Br, 26.25; Cl, 11.63. MS: 269(24), 267(23), 240(63), 238(66), 211(30), 209f34), 130 (85), 56 (100). NMR (DMSOd6): δ0.97 (t, 3H), 1.71 (sextet, 2H), 1.79 sextet, 1H), 2.27 (broad d, 1H), 2.75 (qt, 1H), 2.88 (broad t, 2H), 2.96 (mult, 2H), 3.25 (qt, 1H), 3.48 (broad mult, 1 H), 7.12 (t, 1H), 7.18 (d, 1H), 7.49 (d, 1H), 9.19 (broad s, 2H).

F. (S)-8-Bromo-2-(N-propylamino)tetralin

Hydrogenation of the hydrochloride salt of the S,S diastereomeric amine from Part D in a manner analogous to that described above gave a 94% yield of the hydrochloride salts of the title compound. In this case the crude product showed minor impurities. A small sample was recrystallized from isopropanol for analysis.

OR: $[\alpha]^{25}_D$ −54° (C=10, MeOH ) Analysis: Calculated for $C_{13}H_{18}BrN\cdot HCl$ Theory: C, 51.25; H, 6.29; N, 4.60; Br, 26.23 Cl, 11.64; Found: C, 51.31; H, 6.30; N, 4.41, Br, .26.44; Cl, 11.81. MS: 269(24), 267(23), 240(63), 238(66), 211(30), 209(34), 130 (85) , 56 (100) . NMR (DMSOd$_6$): δ0.97 (t, 3H), 1.71 (sextet, 2H), 1.79 (sextet, 1H), 2.27 (broad d, 1H), 2.75 (qt, 1H), 2.88 (broad t, 2H), 2.96 (mult, 2H), 3.25 (qt, 1H), 3.48 (broad mult, 1H), 7.12 (t, 1H), 7.18 (d, 1H), 7.49 (d, 1H), 9.19 (broad s, 2H)

G. (S)-8-Bromo-N,N-dipropyl-2-aminotetralin

To a solution of (S)-8-bromo-N-propyl-2-aminotetralin (5.0 gm, 18.6 mMol) as produced in Part F in acetonitrile (75 mL) were added n-propyl iodide (3.0 mL, 31 mMol), followed by powdered potassium carbonate (4.0 gm, 29 mMol), and the reaction mixture was stirred for the weekend at 50°. The reaction mixture was then cooled to room temperature and filtered. The filtrate was concentrated in vacuo to give a yellow oil. Purification by flash chromatography (2:1 hexane;diethyl ether+tr. NH$_4$OH) gave the title compound as a colorless oil (3.6 gm, 62%).

NMR (CDCl$_3$): δ7.39 (d, J=8.01 Hz, 1H), 6.98 (m, 2H), 2.90(m, 4H), 2.53(m, 5H), 2.02(m, 1H), 1.50 (M, 5H0, .091 (t, J=7.30 Hz, 6H).

H. (R)-8-Bromo-N,N-dipropyl-2-aminotetralin (R)-8-Bromo-N-propyl-2-aminotetralin (10.5 gm, 39.2 mMol) as produced in Part E was treated as described in Part G to give the title compound as a colorless oil (9.6 gm, 80%). The NMR spectrum recorded for this compound was identical to the spectrum recorded for the compound of Part G.

The synthesis of the compounds of formula I is further illustrated by the following preparative examples. It will be understood by the reader that the following examples are to be read in the light of the chemist's general knowledge and the preceding general teaching, and, in that way, may be used to illustrate the general synthesis all of the present compounds.

EXAMPLES

EXAMPLE 1

(±)-6-Bromo-4-(di-n-propylamino)-1,3,4,5-tetrahydrobenz[c,d]-indazole

A. 8-Bromo-2-tetralone

2-Bromophenylacetyl chloride was prepared from 100 g (0.47 mol) of the corresponding carboxylic acid by heating with an excess of thionyl chloride (50 mL), then removing the excess reagent under vacuum. A solution of the crude acid chloride in 350 mL of dichloromethane was added to a mechanically stirred suspension of 124 g (0.93 mol) of aluminum chloride in 1.5 L of dichloromethane maintained at −60°. A stream of ethylene gas was then passed through the solution for 3 h while continuing to maintain ice bath cooling. The cold reaction mixture was poured onto 3 Kg of crushed ice. The dichloromethane layer was separated from the aqueous layer and washed with 1N hydrochloric acid followed by aqueous sodium bicarbonate. After drying over magnesium sulfate, the dichloromethane was evaporated. The residual oil was dissolved in 1 L of 1:1 dichloromethane/cyclohexane and filtered through Celite. The solvents were removed under vacuum, and the product was recrystallized from cyclohexane/hexane. The yield of crystalline tetralone, mp 79° , was 76.4 g {73%).

B. (±)-8-Bromo-2-(n-propylamino)tetralin

To a cold solution of 100 g (1.69 mol) of 1-propylamine in 2.5 L of acetonitrile was added 10.0 mL (0.175 mol) of acetic acid followed by 11.0 g (0.175 mol) of sodium cyanoborohydride. To this mixture was added 100 g (0.44 mol) of the above tetralone followed by 25 g of 3A molecular sieves. After stirring at room temperature for 2 h, another 16.9 g (0.269 mol) of sodium cyanoborohydride was added followed by 87 mL (1.52 mol) of acetic acid. At 2 hour intervals two additional 30 mL portions of acetic acid were added to the mixture. Stirring was continued for another 16 h, after which the mixture was poured into ice cold 2M sodium hydroxide and extracted with dichloromethane. The extract was filtered, then evaporated to an oily residue. This oil was dissolved in aqueous tartaric acid containing enough methanol to retain the salt in solution. After washing with diethyl ether, the aqueous solution was basified with 2M sodium hydroxide and extracted with dichloromethane. Evaporation of the dichloromethane after drying over sodium sulfate gave 62.5 g (52% yield) of crude product that appeared clean by nuclear magnetic resonance analysis.

C. (±)-8-Bromo-2-(N-n-propyl-N-propionamido)-tetralin

A solution of the above amine (62.5 g, 0.23 mol) in 500 mL of pyridine was treated with 100 mL of propionic anhydride. After stirring at room temperature for several hours, the pyridine and the bulk of the excess anhydride were removed under vacuum. The remainder of the unreacted anhydride was destroyed by stirring with aqueous sodium carbonate solution. The crude amide was extracted into dichloromethane. After drying over sodium sulfate, the dichloromethane was evaporated leaving a quantitative yield of crude amide that was clean by nuclear magnetic resonance analysis.

D. (±)-8-Bromo-5-nitro-2-(N-5-propyl-N-propionamido)-tetralin

To a solution of the above amide (0.23 mol) in 300 mL of chloroform was added 140 mL of trifluoroacetic anhydride followed by 25 g (0.31 mol) of powdered ammonium nitrate. After about 20 min an exothermic reaction ensued. The reaction was moderated by occasional cooling with ice. After the reaction had subsided and all the ammonium nitrate had dissolved, another 5 g of ammonium nitrate was added, and stirring was continued for another 4 h. The solvents were removed under vacuum. The residual oil was diluted with 50 mL of tetrahydrofuran, and added slowly to an ice cold mixture of 250 mL of 1M hydrochloric acid and 250 mL of methanol. The resulting mixture was diluted with 1 L of water and extracted with dichloromethane. The extract was washed with sodium bicarbonate solution until the washings remained basic. After drying over sodium sulfate, the dichloromethane was evaporated leaving a mixture of the 5- and 7-nitro isomers. The isomers were separated by chromatography over silica gel using a gradient starting with toluene and proceeding to 1:9 ethyl acetate/toluene. The 5-nitro isomer from the column crystallized upon standing. After recrystallization from toluene/hexane, the yield of the desired isomer was 37.7 g (46%).

E.
(±)-5-Amino-8-bromo-2-(N-n-propyl-N-propionamido)tetralin hydrochloride A solution of 10.0 g (27.1 mmol) of the 5-nitro compound in 250 mL of ethanol was hydrogenated over 1.0 g of sulfided 5% platinum on carbon at 40 psi. After 4 h the catalyst was removed by filtration. The ethanol was immediately removed under vacuum, and the residue was dissolved in 200 mL of dichloromethane. Treatment of this solution with 15 mL of 2.5M hydrochloric acid in diethyl ether produced the hydrochloride salt as a gummy precipitate. Evaporation of the dichloromethane, and trituration with diethyl ether resulted in a granular solid which, after drying under vacuum at 50°, weighed 10.2 g (Quantitative yield).

F. (±)-8-Bromo-2-(N-n-propyl-N-propionamido)tetralin-5-diazonium tetrafluoroborate A suspension of 10.2 g (27.1 mmol) of the hydrochloride salt of the 5-amino compound in a solution of 30 mL of water and 4.5 mL of conc. hydrochloric acid was stirred at 0° as a solution of 1.30 g (33.4 mmol) of sodium nitrite in 12 mL of water was added dropwise. Stirring at 0° was continued until all the solid dissolved. The resulting turbid, brown solution was then treated with a solution of 4.50 g of sodium tetrafluoroborate in 16 mL of water. The gummy precipitate that resulted gradually crystallized. After chilling for several hours, the salt was collected and washed with cold 5% aqueous sodium tetrafluoroborate followed by a 1:3 mixture of methanol and diethyl ether. The dried salt weighed 8.59 g {72% yield).

G.
(±)-6-Bromo-4-(N-n-propyl-N-propionamido)-1,3,4,5-tetrahydrobenz[c,d]indazole A solution of 4.0 g (9.13 mmol) of the above diazonium salt in 150 mL of chloroform was cooled with ice as 22 mL of an anhydrous 1M solution of tetrabutylammonium fluoride in tetrahydrofuran was slowly added (15 min). After stirring at room temperature for another 2 h, the solution was washed three times with sodium chloride solution. The sodium sulfate dried solution was then evaporated to a viscous oil. Chromatography of this oil over 150 g of silica gel using 1:6 ethyl acetate/toluene followed by 1:1 ethyl acetate/toluene afforded 2.72 g (85% yield) of product that was still contaminated with a small amount of tetrabutylammonium salt.

H.
(±)-6-Bromo-4-(di-n-propylamino-1,3,4,5tetrahydrobenz[c,d]indazole

A solution of 2.68 g (7.66 mmol) of the above indazole in 8 mL of tetrahydrofuran was added slowly to 40 mL of ice-cooled 1M borohydride:tetrahydrofuran. This solution was then refluxed for 1 h. After cooling, the solution was added slowly to 150 mL of acetone. The acetone solution was then refluxed for 2 h. Evaporation of the solvents left a viscous oil. When this oil was taken up in 150 mL of dimethyl sulfoxide containing 3% water, a colorless ppt formed. Heating this mixture at 110° for 20 h produced a clear solution. After cooling the solution and diluting with 500 mL of water, the product was extracted into dichloromethane. The crystalline product left upon evaporation of the dichloromethane was dissolved in 50 mL of water containing 5 g of tartaric acid. The aqueous solution was washed with dichloromethane, basified with 2M sodium hydroxide, and extracted with dichloromethane. After drying over sodium sulfate, the solvent was evaporated. The product, after recrystallization from isooctane, weighed 1.56 g (61% yield), mp 128°–129°.

Analysis: Calculated for $C_{16}H_{22}BrN_3$ Theory: C, 57.15; H, 6.57; N, 12.50 Found: C, 56.87; H, 6.76; N, 12.26 MS: 337 & 335 (M), 308 & 306 (M - $N_2H$)

EXAMPLE 2
(±) -6-Methoxy-4- (di-n-propylamino) -1,3,4,5-tetrahydrobenz [c,d]-indazole To a solution of 0.14 g (6.0 mmol) of sodium in 1.5 mL of methanol was added 5.0 mL of dimethylformamide and 0.15 g (0.8 mmol) of cuprous iodide followed by 0.10 g (0.30 mmol) of the bromoindazoie from Example 1. This mixture was heated under nitrogen at 130° for 5. After cooling, the mixture was filtered. The filtrate was added to ice cold ammonium hydroxide solution, and the product was extracted into dichloromethane. The extract was evaporated to a brown oil. This residue was dissolved in diethyl ether. After washing this solution with sodium chloride solution, the diethyl ether was evaporated and the product was chromatographed over 3 g of Florisil using ethyl acetate. The product from the column was an oil which crystallized when triturated with hexane. Recrystallization from isooctane afforded 0.069 g (80% yield) of colorless product, mp 109°–111°.

Analysis: Calculated for $C_{17}H_{25}N_3O$ Theory: C, 71.05; H, 8.77; N, 14.62 Found: C, 71.32; H, 8.74; N, 14.66 MS: 287 (M) , 258 (M - $N_2H$)

EXAMPLE 3
(±)-6-Cyano-4-(di-n-propylamino)-1,3,4,5-tetrahydrobenz[c,d]-indazole A stream of nitrogen was used to displace dissolved air from 10 mL of dimethylformamide, after which 0.30 g (0.89 mmol) of the bromoindazole from Example 1, 0.25 g of cuprous cyanide, and 0.50 g of cuprous iodide were added. This mixture was heated under nitrogen at 130° for 22 h. After cooling, the mixture was shaken with conc. ammonium hydroxide and dichloromethane. The resulting emulsion was allowed to stand for several hours until the layers fully separated. The dichloromethane layer was then washed three times with fresh conc. ammonium hydroxide. The dichloromethane was evaporated, and the residue was dissolved in dilute tartaric acid. The pH of the aqueous solution was raised to 3.5 by careful addition of 1M sodium hydroxide. The resulting suspension was filtered through Celite, rinsing the precipitate with fresh water. The clear, yellow filtrate was basified with 5M sodium hydroxide, and the product was extracted into dichloromethane. Evaporation of the dichloromethane left 0.16 g of a light brown oil that slowly crystallized. Chromatography of this material over 3 g of silica gel using successively 1:9, 2:3, and 3:7 ethyl acetate/toluene provided 0.13 g (52% yield) of crystalline product, mp 118°–119°.

Analysis: Calculated for $C_{17}H_{22}N_4$ Theory: C, 72.31; H, 7.85; N, 19.84 Found: C, 72.14; H, 7.89; N, 19.72 MS: 282 (M), 253 (M - $N_2H$)

EXAMPLE 4

(±)-4- (Di-n-propylamino) -1,3,4,5-tetrahydrobenz [c,d]indazole-6-carboxamide

A. (±)-6-Bromo-1-triisopropylsilyl-4-(di-n-propylamino) -1,3,4,5-tetrahydrobenz [c,d]indazole A suspension consisting of 0.32 g (1.6 mmol) of a 20% dispersion of potassium hydride in mineral oil and 15 mL of tetrahydrofuran was stirred at 0° as 0.50 g (1.49 mmol) of the product from Example 1 was added. After 30 min the cold solution was treated with 0.48 mL (0.55 g, 1.79 mmol) of triisopropylsilyl triflate. After another hour, the mixture was poured into cold, dilute sodium bicarbonate solution. The crude product was extracted into dichloromethane. The solvent was removed, and the product was chromatographed over 15 g of silica gel using toluene followed by 1:1 ethyl acetate/toluene. Evaporation of the solvents gave an oil that crystallized upon standing. The product was taken up in hexane. The hexane solution was filtered, and the hexane was evaporated leaving 0.69 g (94% yield) of crystalline product, mp 79°–82°.

B. (±)-1-Triisopropylsilyl-4- (di-! 1-propylamino)-1,3,4,5-tetrahydroben[c,d]indazole-6-carboxamide A solution of 0.30 g (0.61 mmol) of the above silylated compound in 10 mL of diethyl ether was treated at −78° with 0.90 mL (1.39 mmol) of 1.54 M tert-butyllithium in pentane. After 30 min, an addition of 0.25 mL (1.85 mmol) of trimethylsilyl isocyanate was made. Stirring at −78° was continued another 15 min, then the solution was allowed to warm to room temperature. It was poured into water, and the product was extracted into diethyl ether. After drying over sodium sulfate, the diethyl ether was evaporated leaving 0.30 g of crude product that was clean by nuclear magnetic resonance analysis.

C. (±)-4-(Di-n-propylamino)-1,3,4,5-tetrahydrobenz[c,d]indazole-6-carboxamide The crude product from the previous step was dissolved in 5 mL of tetrahydrofuran, cooled to 0°, and treated with 1.0 mL of 1M tetrabutylammonium fluoride in tetrahydrofuran. After 20 min, the solution was poured into aqueous tartaric acid solution (1 g in 30 mL). This aqueous solution was washed with dichloromethane, basified with 2M sodium hydroxide, and extracted with dichloromethane. The sodium sulfate dried solution was evaporated, and the residue was chromatographed over 5 g of Florisil using 3% methanol in ethyl acetate. Trituration of the product with toluene afforded 0.127 g (70% yield) of crystalline (±)-4-(di-n-propylamino)-1,3,4,5-tetrahydrobenz[c,d]indazole-6-carboxamide, mp 203°–204°.

Analysis: Calculated for $C_{17}H_{24}N_4O$ Theory: C, 67.97; H, 8.05; N, 18.65 Found: C, 68.26; H, 7.84; N, 18.88 MS (FD): 300 (M)

EXAMPLE 5

(±)-Methyl 4-(di-n-propylamino)-1,3,4,5-tetrahydrobenz[c,d]-indazole-6-carboxylate

A. (±)-1-Triisopropylsilyl-4-(di-n-propylamino)-1,3,4,5-tetrahydrobenz[c,d]indazole-6-carboxylic acid A solution of 0.50 g (1.00 mmol) of (±)-6-bromo 1-triisopropylsilyl-4-(di-n-propylamino)-1,3,4,5-tetrahydrobenz[c,d]indazole (Example 4-A) in 15 mL of diethyl ether was cooled to −70°, then treated with 1.5 mL (2.3 mmol) of 1.54M tert-butyllithium in pentane. After stirring the solution for 30 min, a stream of carbon dioxide was bubbled through it for 5 min. The solution was allowed to warm to room temperature. It was then poured into 50 mL of water and shaken. The pH of the aqueous layer was lowered to 6.8 using 1N hydrochloric acid, and the mixture was again shaken. The diethyl ether layer was separated. The aqueous layer was further extracted with dichloromethane. The combined organic layers were dried over sodium sulfate, then evaporated. The crude product was chromatographed over 5 g of Florisil eluting successively with 1:1 ethyl acetate/toluene, ethyl acetate, and 1:9 methanol/ethyl acetate. The purified product was a faintly blue oil that crystallized on standing. The product weighed 0.28 g (61% yield).

B. (±)-Methyl4-(di-n-propylamino)-1,3,4,5tetrahydrobenz[c,d]indazol-6-carboxylate A solution of 0.24 g (0.53 mmol) of the above carboxylic acid and 0.13 g (0.75 mmol) of 1,1′-carbonyldiimidazole in 2.5 mL of tetrahydrofuran was heated at 55° for 6 h. An addition of 2.5 mL of methanol was made, and heating was continued another 15 h. The solution was added to water, and the product was extracted into dichloromethane. After drying over sodium sulfate the dichloromethane was evaporated leaving 0.19 g of partially desilylated ester. Desilylation was completed by treating a solution of the product in 5 mL of tetrahydrofuran at 0° with 0.30 g of finely powdered boric acid followed by 0.5 mL of 1 M tetrabutylammonium fluoride in tetrahydrofuran. After 30 min the mixture was added to dilute sodium bicarbonate solution, and the product was extracted into dichloromethane. The dichloromethane solution was then extracted with dilute aqueous tartaric acid solution (0.5 g/20 mL). The aqueous extract was basified with sodium carbonate solution, and the product was extracted into dichloromethane. The ester was further purified by chromatography over 4 g of silica gel using 1:9 ethyl acetate/toluene followed by recrystallization from toluene/hexane. The purified ester weighed 0.094 g (56% yield), mp 131°–2°.

Analysis: Calculated for $C_{18}H_{25}N_3O_2$ Theory: C, 68.52; H, 7.99; N, 13.32 Found: C, 68.78; H, 7.84; N, 13.29 MS (FAB): 316.5 (M +1)

EXAMPLE 6

(±)-6-Acetyl-4- (di-n-propylamino) -1,3,4,5-tetrahydrobenz[c,d]indazole

A. (±)-6-(1-Hydroxyethyl)-1-triisopropylsilyl-4-(di-n-propylamino)-1,3,4,5-tetrahydrobenz[c,d]indazole A solution of 0.50 g (1.00 mmol) of (±)-6-bromo-1-triisopropylsilyl-4-(di-n-propylamino)-1,3,4,5-tetrahydrobenz[c,d]indazole (Example 4-A) in 15 mL of diethyl ether was cooled to −70°, then treated with 1.5 mL (2.3 mmol) of 1.54M tert-butyllithium in pentane. After stirring for 30 min an addition of 0.25 mL of acetaldehyde was made, and the solution was allowed to warm to room temperature. The solution was poured into water, and the product was extracted into diethyl ether. After drying over sodium sulfate the diethyl ether was evaporated. The residual oil was chromatographed over 5 g of silica gel using toluene followed by 1:9 ethyl acetate/toluene. The purified alcohol was a viscous oil weighing 0.47 g.

B. (±)-6-Acetyl-4- (di-n-propylamino)-1,3,4,5-tetrahydrobenz[c,d]indazole

A solution of 0.40 g (0.88 mmol) of the above alcohol in 10 ml of dichloromethane was cooled to 0°, then treated with 0.50 g (1.33 mmol) of pyridinium dichromate. After stirring at 0° for 2.5 h the mixture was diluted with 10 mL of diethyl ether and filtered through Celite. The solvents were removed, and the residual oil was chromatographed over 5 g of Florisil using toluene followed by 1:9 ethyl acetate/toluene. The partially desilylated product weighed 0.21 g. Desilylation was completed as described in Example 5-B. Chromatography over 4 g of silica gel using 1:1 ethyl acetate/toluene followed by recrystallization from toluene/hexane resulted in 0.057 g (22% yield) of (±)-6-acetyl-4-(di-n-propylamino)-1,3,4,5-tetrahydrobenz[c,d]indazole, mp 107°–8°.

Analysis: Calculated for $C_{18}H_{25}N_3O$ Theory: C, 72.21; H, 8.42; N, 14.03 Found: C, 72.05; H, 8.42; N, 13.81 MS(FAB): 300.3 (M+1)

BIOLOGICAL ACTIVITY

The present compounds of Formula I have been found to have selective affinity for the serotonin (5HT) receptors in the brain with much less affinity for other receptors. Because of their ability to selectively bind to 5-HT receptors, the compounds of Formula I are useful in treating disease states which require alteration of 5-HT receptor function, particularly 5-HT$_{1A}$ and/or 5HT$_{1D}$ but without the side effects which may be associated with less selective compounds. This alteration may involve reproducing (an agonist) or inhibiting (an antagonist, particularly agonist activity, the function of serotonin. These disease states include anxiety, depression, excessive gastric acid secretion, motion sickness, hypertension, nausea and vomiting, sexual dysfunction, cognition, senile dementia, migraine, consumptive disorders such as appetite disorders, alcoholism and smoking. The foregoing conditions are treated with a pharmaceutically effective amount of a compound of Formula I or a pharmaceutically acceptable salt thereof.

The term "pharmaceutically effective amount", as used herein, represents an amount of a compound of the invention which is capable of diminishing the adverse symptoms of the particular disease. The particular dose of compound administered according to this invention shall, of course, be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical single dose for treatment, however, will contain from about 0.01 mg/kg to about 50 mg/kg of the active compound of this invention when administered orally. Preferred oral doses will be about 0.01 to about 3.0 mg/kg, ideally about 0.01 to about 0.1 mg/kg. When a present compound is given orally it may be necessary to administer the compound more than once each day, for example about every eight hours. For IV administration by bolus, the dose will be from about 10 μg/kg to about 300 μg/kg, preferably about 20 μg/kg to about 50 μg/kg.

The following test methods were used to demonstrate the ability of the compounds of Formula I to bind to 5-HT receptors. Such experiments demonstrate the utility of the compounds of Formula I in treating disease states (such as those noted above which require alteration of the 5-HT receptor function.

The affinities of certain of the compounds of Formula I at the central 5-HT$_{1A}$ receptors were determined using a modification of the binding assay described by Taylor, et al., *J. Pharmacol. ExD. Ther.*, 236, 118–125 (1986). Membranes for the binding assay were prepared from male Sprague-Dawley rats (150–250 g). The animals were killed by decapitation, and the brains were rapidly chilled and dissected to obtain the hippocampi. Membranes from the hippocampi were either prepared that day, or the hippocampi were stored frozen (−70°) until the day of preparation. The membranes were prepared by homogenizing the tissue in 40 volumes of ice-cold Tris-HCl buffer (50 mM, pH 7.4 at 22°) using a Techmar Tissumizer (setting 65 for 15 seconds), and the homogenate was centrifuged at 39800 xg for 10 minutes. The resulting pellet was then resuspended in the same buffer, and the centrifugation and resuspension process was repeated three additional times to wash the membranes. Between the second and third washes the resuspended membranes were incubated for 10 minutes at 37° to facilitate the removal of endogenous ligands. The final pellet was resuspended in 67 mM Tris-HCl, pH 7.4, to a concentration of 2 mg of tissue original wet weight/200 μl. This homogenate was stored frozen (−70°) until the day of the binding assay. Each tube for the binding assay had a final volume of 800 μl and contained the following: Tris-HCl (50 mM), pargyline (10 μM), CaCl$_2$ (3 mM), [$^3$H]8—OH—DPAT (1.0 nM), appropriate dilutions of the drugs of interest, and membrane resuspension equivalent to 2 mg of original tissue wet weight, for a final pH of 7.4. The assay tubes were incubated for 10 minutes at 37°, and the contents were then rapidly filtered through GF/B filters (pretreated with 0.5% polyethylenimine), followed by four 1 ml washes with ice-cold buffer. The radioactivity trapped by the filters was quantitated by liquid scintillation spectrometry, and specific [$^3$H]8—OH—DPAT binding to the 5-HT$_{1A}$ sites was defined as the difference between [$^3$H]8—OH—DPAT bound in the presence and absence of 10 μM 5-HT.

The results of the evaluation of various compounds of Formula I in the test system described above demonstrate that the compounds have a high degree of activity which clearly predicts their therapeutic usefulness.

The affinities of certain of the compounds of Formula I at the central 5-HT$_{1D}$ binding sites were determined using a modification of the binding assay described by Heuring and Peroutka, *J. Neurosci.*, 7, 894 (1987). Bovine brains were obtained and the caudate nuclei were dissected out and frozen at $-70°$ until the time that the membranes were prepared for the binding assays. At that time the tissues were homogenized in 40 volumes of ice-cold Tris-HCl buffer (50 mM, pH 7.4 at 22°) with a Techmar Tissumizer (setting 65 for 15 seconds), and the homogenate was centrifuged at 39,800 xg for 10 minutes. The resulting pellet was then resuspended in the same buffer, and the centrifugation and resuspension process was repeated three additional times to wash the membranes. Between the second and third washes the resuspended membranes were incubated for 10 minutes at 37° to facilitate the removal of endogenous 5-HT. The final pellet was resuspended in Tris buffer to a concentration of 25 mg of original tissue wet weight/ml for use in the binding assay. Each tube for the binding assay had a final volume of 800 μl and contained the following: Tris-HCl (50 mM), pargyline (10 μM), ascorbate (5.7 mM), CaCl$_2$ (3 mM), 8—OH—DPAT (100 nM to mask 5-HT$_{1A}$ receptors), mesulergine (100 nM to mask 5-HT$_{1c}$ receptors), [$^3$H]5-HT (1.7–1.9 nM), appropriate dilutions of the drugs of interest, and membrane resuspension equivalent to 5 mg of original tissue wet weight, for a final pH of 7.4. The assay tubes were incubated for 10 minutes at 37°, and the contents were then rapidly filtered through GF/B filters (pretreated with 0.5% polyethylenimine), followed by four 1 ml washes with ice-cold buffer. The radioactivity trapped by the filters was quantitated by liquid scintillation spectrometry, and specific [$^3$H]5-HT binding to the 5-HT$_{1D}$ sites was defined as the difference between [$^3$H]5-HT bound in the presence and absence of 10 μm 5-HT.

The results of the evaluation of various compounds of Formula I in the test system described above show that the compounds have an unusual amount of activity at the 5-HT$_{1D}$ receptor, and accordingly are highly biologically active for the purposes described here.

In another test certain compounds of Formula I were evaluated to determine ability to affect serotonin turnover in vivo. As a measure of such effect on serotonin turnover, the decrease of the serotonin metabolite 5-hydroxyindoleacetic acid (5HIAA) was measured. The following protocol was employed.

Male albino rats were dosed either subcutaneously or orally with an aqueous solution of the compound tested. The pH of the solution was adjusted as necessary to solubilize the compound. A control of the solution without the test compound was similarly administered to a control animal. The rats were decapitated one hour later. The whole brain was then removed and frozen on dry ice for storage prior to analysis. 5-Hydroxyindoleacetic acid (5HIAA) concentration in whole brain was measured by liquid chromatography with electrochemical detection as reported by Fuller and Perry, "Effects of Buspirone and its Metabolite, 1-(2-pyrimidinyl)piperazine, on Brain Monoamines and Their Metabolites in Rats", *J. Pharmacol. Exp. Ther.*, 248, p. 50–56 (1989).

The serotonin turnover tests demonstrated, as expected from the other tests, that compounds of formula I significantly lower the turnover of 5-HT in whole brain of the intact test animals.

Some compounds were also tested in ligated pylorus rats to evaluate their effect on basal acid secretion, an important physiological effect which is mediated by the 5-HT$_{1A}$ receptor.

The pylorus ligated rat model used in a modification of the procedure developed by Shay (Shay, H., Komarov, A. A. and Greenstein, M.: "Effects of vagotomy in the rat." *Arch. Surg.*, 49: 210–226, 1949). Male Sprague-Dawley rats weighing approximately 200 g were starved 24 hours prior to using, with water allowed ad libitum. Under light ether anesthetic the pylorus is ligated, simultaneously the rat is dosed intraperitoneally (i.p.) or subcutaneously (s.c.) and allowed 2 hours for stomach acid accumulation. At the end of 2 hours the rats are sacrificed. Stomach content is measured and titrated to a pH end point of 7.0. Each experiment has its own control group for determining percent of acid change over the 2-hour time period.

Specific compounds within the scope of the above general classes of direct acting 5-HT1A agonists were tested. For evaluation purposes, the compound to be tested is dissolved in distilled water, or in 10% dimethyl sulfoxide, pending upon its solubility. The results of the test demonstrate that the tested compounds significantly inhibit the secretion of gastric acid, clearly indicating therapeutic effect for patients having or at risk of having gastric ulcers.

COMPOSITIONS

The compounds of the present invention are preferably formulated prior to administration. Therefore, yet another embodiment of the present invention is a pharmaceutical formulation comprising a compound of the invention and a pharmaceutically acceptable excipient therefor.

The present pharmaceutical formulations are prepared by known procedures using well known and readily available ingredients. In making the compositions of the present invention, the active ingredient will usually be mixed with an excipient, diluted by an excipient or enclosed within an excipient serving as a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl and propylhydroxybenzoates, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 0.5 to about 50 mg, more usually about 1 to about 10 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| (−)-6-(2-oxazolyl)-4-(di-n-propylamino)-1,3,4,5-tetrahydrobenz[cd]indazole | 25 |
| Starch, dried | 425 |
| Magnesium stearate | 10 |
| Total | 460 mg |

The above ingredients are mixed and filled into hard gelatin capsules in 460 mg quantities.

FORMULATION 2

A tablet formula is prepared using the ingredients below:

|  | Quantity (mg/tablet) |
|---|---|
| (±)-6-[3-(5-aminothiazolyl)]-4-(di-n-propylamino)-1,3,4,5-tetrahydrobenz[cd]indazole | 25 |
| Cellulose, microcrystalline | 625 |
| Colloidal silicon dioxide | 10 |
| Stearic acid | 5 |

The components are blended and compressed to form tablets each weighing 665 mg.

FORMULATION 3

A dry powder inhaler formulation is prepared containing the following components:

|  | Weight % |
|---|---|
| (±)-6-(5-isoxazolyl)-4-(di-n-propylamino)-1,3,4,5-tetrahydrobenz[cd]indazole | 5 |
| Lactose | 95 |

The active compound is mixed with the lactose and the mixture added to a dry powder inhaling appliance.

FORMULATION 4

Tablets each containing 60 mg of active ingredient are made up as follows:

|  |  |
|---|---|
| (+)-6-(2-pyrazolyl)-4-(di-n-propylamino)-1,3,4,5-tetrahydrobenz[cd]indazole | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°–60° C. and passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

FORMULATION 5

Capsules each containing 20 mg of medicament are made as follows:

|  |  |
|---|---|
| (±)-6-(5-oxadiazolyl)-4-(dimethylamino)-1,3,4,5-tetrahydrobenz[cd]indazole | 20 mg |
| Starch | 169 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

FORMULATION 6

Suppositories each containing 225 mg of active ingredient are made as follows:

|  |  |
|---|---|
| (+)-6-carboxamido-4-(di-n-propylamino)-1,3,4,5-tetrahydrobenz[cd]indazole | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

|  |  |
|---|---|
| (±)-6-methoxycarbonyl-4-(di-n-propylamino)-1,3,4,5-tetrahydrobenz[cd]indazole | 50 mg |
| Xanthan gum | 4 mg |
| Sodium carboxymethyl cellulose (11%) Microcrystalline cellulose (89%) | 50 mg |
| Sucrose | 1.75 g |
| Sodium benzoate | 10 mg |
| Flavor | q.v. |
| Color | q.v. |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume.

FORMULATION 8

Capsules each containing 50 mg of medicament are made as follows:

| | |
|---|---|
| (+)-6-acetyl-4-(dimethyl-amino)-1,3,4,5-tetrahydrobenz[cd]-indazole | 50 mg |
| Starch | 507 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules.

I claim:

1. A compound of the formula

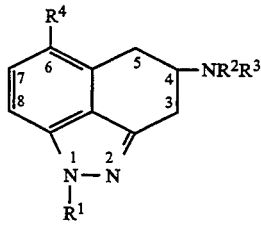

I $R^1$ is hydrogen, $C_1$–$C_4$ alkyl or a blocking group;
$R^2$ is hydrogen, $C_1$–$C_4$ alkyl, $C_3$–$C_4$ alkenyl, cyclopropylmethyl or aryl-($C_1$–$C_4$ alkyl);
$R^3$ is hydrogen, $C_1$–$C_4$ alkyl, $C_3$–$C_4$ alkenyl, or cyclopropylmethyl;
$R^4$ is X-$R^5$ halo cyano, $C_1$–$C_3$ alkoxy, benzyloxy or acyloxy;

X is CO or CHOH;
$R^5$ is hydrogen, $C_1$–$C_8$ alkyl, substituted $C_1$–$C_8$ alkyl, $C_1$–$C_4$ alkoxy, $C_1$–$C_4$ alkylthio, aryl, substituted aryl, aryl-($C_1$–$C_4$ alkyl), substituted aryl-($C_1$–$C_4$ alkyl), ($C_3$–$C_7$ cycloalkyl)-methyl, $NR^6R^7$, or $C_3$–$C_7$ cycloalkyl;
$R^6$ and $R^7$ are independently hydrogen, $C_1$–$C_4$ alkyl, phenyl-($C_1$–$C_4$ alkyl), phenyl, or together with the nitrogen atom to which they are attached form a $C_3$–$C_5$ heterocyclic ring;
and the pharmaceutically acceptable salts thereof.

2. A compound of claim 1 wherein $R^2$ is hydrogen, alkyl, alkenyl or cyclopropylmethyl.

3. A compound of claim 2 wherein $R^3$ is hydrogen, alkyl or alkenyl.

4. A compound of claim 1 wherein $R^1$ is hydrogen or a blocking group.

5. A compound of claim 1 wherein $R^4$ is halo or alkoxy.

6. A compound of claim 1 wherein $R^4$ is X-$R^5$.

7. A compound of claim 3 wherein $R^1$ is hydrogen or a blocking group.

8. A compound of claim 7 wherein $R^4$ is halo or alkoxy.

9. A compound of claim 1 wherein both $R^2$ and $R^3$ are alkyl.

10. A compound of claim 9 wherein $R^1$ is hydrogen or a blocking group.

11. A compound of claim 10 wherein $R^4$ is halo or alkoxy.

12. A pharmaceutical composition comprising a compound of claim 1 wherein $R^1$ is hydrogen or $C_1$–$C_4$ alkyl and a pharmaceutically acceptable excipient.

13. A method of regulating a serotonin receptor comprising administering an effective amount of a compound of claim 1 wherein $R^1$ is hydrogen or $C_1$–$C_4$ alkyl to a patient in need thereof.

14. A method of claim 13 wherein the serotonin receptor is the 5-$HT_{1A}$ receptor.

15. A method of claim 13 wherein the serotonin receptor is the 5-$HT_{1D}$ receptor.

* * * * *